(12) United States Patent
Sardjiman et al.

(10) Patent No.: US 6,541,672 B1
(45) Date of Patent: Apr. 1, 2003

(54) DERIVATIVES OF BENZILIDINE CYCLOHEXANONE, BENZILIDINE CYCLOPENTANONE, AND BENZILIDINE ACETONE AND THEIR SYNTHESIS

(75) Inventors: p## Sardjiman, Yogyakarta (ID); Mochammad Samhoedi Reksohadiprodjo, Yogyakarta (ID); Henk Timmerman, Amsterdam (NL)

(73) Assignee: Faculty of Pharmacy, The University of Gadjah Mada, Yogyakarta (ID)

( * ) Notice: Subject to any disclaimer, the term of this patent is extended or adjusted under 35 U.S.C. 154(b) by 0 days.

(21) Appl. No.: 09/026,624

(22) Filed: Feb. 20, 1998

(30) Foreign Application Priority Data

Feb. 20, 1997 (ID) ................................................. 970482

(51) Int. Cl.[7] ............................................. C07C 49/563
(52) U.S. Cl. ........................ 568/308; 568/313; 568/345; 568/376; 568/379
(58) Field of Search ................................ 568/308, 309, 568/313, 326, 338, 343, 345, 376, 379

(56) References Cited

U.S. PATENT DOCUMENTS 3,389,986 A * 6/1968 Bella ............................ 71/123
4,552,876 A 11/1985 Jones et al. ................. 514/234

FOREIGN PATENT DOCUMENTS

DE 2009504 * 9/1971

OTHER PUBLICATIONS

Borden et al, Journal of Applied Polymer Science, 22(1), pp. 239–251 1978.*
Chem.Ind. (London), vol. 21, pp. 685–686 1970.*
N.P. Buu–Hoi et al., "Condensation product of cyclic ketones with aromatic amine aldehydes and their choleretic activity," Chem. Abstrs., vol. 60, 10589h (1964).
E.P. Dibella, "2,6–Dibenzylidenecyclohexanones," Chem. Abstrs., vol. 69, p. 4830 (1968).

O. Gisvold et al., "Synthesis of some α,ω–bis(,4–dihydroxyphenyl)alkanes.," Chem. Abstrs., vol. 40, 6451[8] (1946).
B.A. Hathaway, "An aldol condensation experiment using a number of aldehydes and ketones," *J. Chem. Education*, vol. 64, pp. 367–368 (Apr. 1987).
P.T. Mora et al., "Disalicylideneacetone and analogs," *Chem. Abstrs.*, vol. 44, 9959d (1950).
W. Rumpel, "Divanillylidenecyclohexanone," *Chem. Abstrs.*, vol. 49, 14802g (1995).
L.C. Raiford et al., "Condensation of 4–dimethylaminobenzalde hyde with vanillalacetone and vanillalacetone derivatives," Chem. Abstrs., vol. 32, 7432[4] (1938).
S. S. Sardjiman et al., "1,5–diphenyl–1, 4–pentadiene–3–ones and cyclic analogues as antioxidative agents. Synthesis and structure–activity relationship," *Eur. J. Med. Chem.*, vol. 32, pp. 625–630 (1997).
H. Whitmann, "Cleavage by means of diazonium compounds and quinone imide chloride. IV. Effects alonga saturated carbon chain," *Chem. Abstrs.*, vol. 60, 439f, 1963.

* cited by examiner

*Primary Examiner*—Sreeni Padmanabhan
(74) *Attorney, Agent, or Firm*—Lahive & Cockfield, LLP; Giulio A. DeConti, Jr.; Peter C. Lauro

(57) ABSTRACT

The invention deals with the derivatives of benzilidine having basic formula as follows (I):

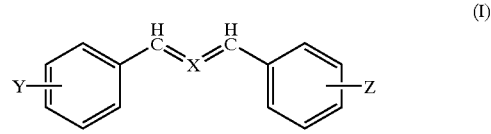

wherein X can be cyclohexanone, cyclopentanone, or acetone, while Y and Z can be either electron withdrawing, electron donating or steric group. Y may or may not be the same with Z. Methyl, ethyl, methoxy group or halogen were prefered in the experiment. The benzilidine cyclohexanone, benzilidine cyclopentanone, and benzilidine acetone derivates were found to be novel compounds showing antibacterial, antioxidant, and anti-inflammatory activities that enable them to be used for drug.

18 Claims, No Drawings

DERIVATIVES OF BENZILIDINE CYCLOHEXANONE, BENZILIDINE CYCLOPENTANONE, AND BENZILIDINE ACETONE AND THEIR SYNTHESIS

TECHNICAL FIELD OF THE INVENTION

The invention relates to benzilidine derivatives, more particular to the synthesis of benzilidine cyclohexanone, benzilidine pentanone, and benzilidine acetone, that showed pharmacological activity as bactericides, anti-oxidant, and anti-inflammation.

BACKGROUND OF THE INVENTION

The invention was initiated by the fact that curcumin with the following formula (II) was widely used for medication as anti-inflammation, anti-bacteria, antioxidant, anti-hepatotoxic, hypocholesterolaemia, anti-cyclooxygenase, anti-cancer, and radical scavanger. However, it was reported that curcumin was unstable in an alkali solution (pH >6.5).

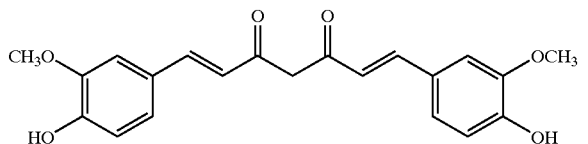

In the mean time the use of aminophyrin as an anti-inflammatory was reported unsave as this compound could produce nitrosamine known as carcinogen. Another pyrazolone derivate (dipyron) was also known, to give adverse side effects such as agranulocytosis and allergic reaction. Similar side effects were also indicated by pyrazolone derivates (phenazone, oxyphenbutazone, phenylbutazone, etc.).

Pharmacological and toxicological profile of phenylbutazone and its derivates can be illustrated below (J. Phar. Pharmacol., 1955, 7, 1002).

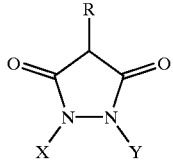

Structure of pyrazolone derivates

| Substituent | Anti inflammation activity (3 × 50 mg/kg) | Acut toxicity (rat), LD 50 g/kg | | |
|---|---|---|---|---|
| | | Oral | Subcutan | Intra peritoneal |
| R = n-butyl R = Y = phenyl (Phenylbutazon) | +++ | 0.73 | 0.23 | 0.23 |
| R = allyl/propyl X = Y = phenyl | +++ | | ∞ | |
| R = n-butyl R = Y = p-CH$_3$—C$_6$H$_4$ | +++ | | Toxicity decrease | |
| R = n-butyl R = Y = p-COOH—C$_6$H$_4$ | + | 8 | 8 | 8 |
| R = n-butyl | + | — | — | — |

Structure of pyrazolone derivates

| Substituent | Anti inflammation activity (3 × 50 mg/kg) | Acut toxicity (rat), LD 50 g/kg | | |
|---|---|---|---|---|
| | | Oral | Subcutan | Intra peritoneal |
| X = H, Y = phenyl R = n-butyl X = Y = (3-OH, 4 carboxy)phenyl Cyclopentanone | | | | |

On the basic the above information a research group at the faculty of Pharmacy GM focused their study using curcumin as lead compound in the order to obtain a potent anti-inflammatory agent which are more stable than curcumin and less toxic compared that of pyrazolone derivates.

SUMMARY OF THE INVENTION

Modification of the center part of curcumin using electron withdrawing as well as electron donating group gave some novel compounds as derivates of benzilidine cyclohexanone, benzilidine cyclopentanone, and benzilidine acetone. The products were proposed under the following patent names:

1. Hexagamavunone

Hexa indicates that center part of the structure is a six-member ring system, gama means Gadjah Mada, vu means Vrije Universiteit, and none indicates that the product is a ketone.

2. Pentagamavunone

Penta indicates that center part of the structure is a five-member ring system, gama means Gadjah Mada, vu means Vrije Universiteit, and none indicates that the product is a ketone.

3. Gamavutone

Gama means Gadjah mada, vu means Vrije Universiteit, and tone indicates that the product contains acetone group at the center of the molecular structure.

The process is also patented under the name of SAMTI-SAR meaning the process was invented by Samhoedi, Timmerman, and Sardjiman.

DETAILED DESCRIPTION OF THE INVENTION

The discovery deals with new compound derivates which have general structure:

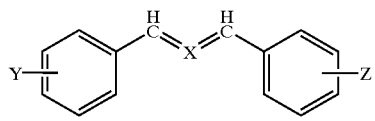

wherein X can be a six-ring alkane derivates, a five-ring with one carbonyl group, or aliphatic group such as acetone; Y and Z can be various different groups: methyl, ethyl, isoprophyl, tertiary butyl, hydroxy, chloro, trifluoro methyl and dimethylamine.

The nominating groups were those with medium steric factor, positive resonance, and negative induction. Several with strong negative induction. Also, the most suitable bis-form is considered.

Chemical structure (I) may be prepared by aldol condensation between structures (II) and (III):

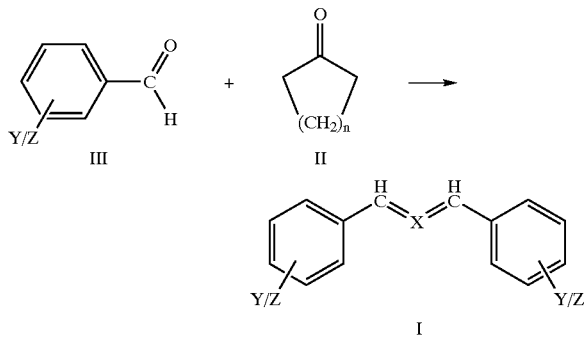

For structure II, n=0–3.

Reaction between (II) and (III) was conducted using common procedures in chemical synthesis, namely aldol condensation, with or without organic solvents. Generally the reaction utilizes suitable organic solvents such as THF or sometimes alcohol. It may be beneficial to add an acid or an alkaline (HCl or NaOH) to the mixture to accelerate the reaction time.

Temperature and length of reaction are a key factor to the reaction. Temperature between 0-50° C. is considered the most suitable.

A good reaction procedure was done refluxing two reactants for several hours, and yield was left for several days. The reaction may be explained as follows:

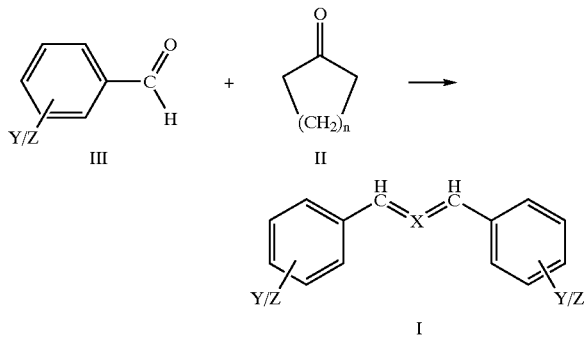

Methods of isolation and purification of the reaction yield were done by washing and recrystallization before elucidation of chemical structure by IR Spectrometer, NMR and Mass Spectrometer. Compounds with chemical structure (I) were recognized as those which are active as antioxidants, and pharmacologically active against inflammation, bacteria and fungi such as C. albicans, S. pneumoniae, S. aureus, and B. subtilis. The structure (I) has been observed to have a strong anti-inflammatory action as explained from the following finding:

ANTI INFLAMMATORY ACTIVITY TEST (WINTER, 1962)

Carragenin was used as an inflammatory agent. The volum inhibition of rat paw edema following peroral administration of various doses of the sysnthetic compounds in 1% CMC in comparison to that of control was used to determine the activity of the compounds. In order to evaluate the anti-inflammatory of each compound. Wistar rats (body weight ranging from 200-250 g) were used and divided randomly into 5 groups: one group served as or control and 4 groups were treatment groups. The control group received the vehicle CMC; (Carboxy Methyl Cellulose 2%), while the treatment groups received the synthetic compound per orally in CMC 1%. Doses of 10, 20, 40 and 80 mg/kg bw were given to the animals. Where one hour later the animals received a subplantar injection of 0.05 ml of carragenin suspension in saline solution (NaCi 0.9%)- The volumes of rat paw edema were measured immediately and every half an hour following the subplantar injection for 5 hours.

ANTI INFLAMMATORY ACTIVITY HEXAGAMAVUNONE (HGV)

| Molecule | $R^1$ | $R^2$ | $R^3$ | ED 50 mg/kg.bb |
|---|---|---|---|---|
| HGV-1 | $CH_3$ | OH | $CH_3$ | 41 |
| HGV-2 | $C_2H_5$ | OH | $C_2H_5$ | 20 |
| HGV-5 | $OCH_3$ | OH | $OCH_3$ | 222 |
| HGV-6 | Cl | OH | Cl | 25 |

PENTAGAMAVUNONE (PGV)

| Molecule | $R^1$ | $R^2$ | $R^3$ | ED 50 mg/kg.bb |
|---|---|---|---|---|
| PGV-1 | $CH_3$ | OH | $CH_3$ | 86 |
| PGV-2 | $C_2H_5$ | OH | $C_2H_5$ | 80 |
| PGV-5 | $OCH_3$ | OH | $OCH_3$ | 48 |
| PGV-6 | Cl | OH | Cl | 20 |
| PGV-0 | $OCH_3$ | OH | $OCH_3$ | 25 |

GAMAVUTONE (GVT)

| Molecule | $R^1$ | $R^2$ | $R^3$ | ED 50 mg/kg.bb |
|---|---|---|---|---|
| GVT-6 | Cl | OH | Cl | — |

ANTI OXIDATION TEST (HAENEN AND BAST, 1983)

Anti oxidative activity (lipid peroxidation) was determined by measuring the reactive form of thiobarbituric acid, i.e. malondialdehyde. The synthetic compound with final concentration of 0.5; 1.0; 2.0; 4.0 microM was put into glass tubes. Solution of tris-HCl/KCl (50 microM/150 microM, pH 7.4), vitamin C (0.5 ml 200 microM) and microsome (final concentration of 2 mg protein/ml). The mixture was pre-incubated at 37° C. for 5 minutes. Lipid peroxidation was initiated with the addition of ferro sulphate (0.5 ml, 10 microN) and incubated at 37° C. for 5 minutes, the reaction was stopped by addition of aliquot (0.3 ml) to the mixture of TCA, TBA, and BHT (2 ml) in cold. After heating (80° C.) for 15 minutes and centrifugation (15 minutes), absorbance was read at 535 nm.

| Molecule | $R^1$ | $R^2$ | $R^3$ | IC 50 (microM) |
|---|---|---|---|---|
| HGV-1 | $CH_3$ | OH | $CH_3$ | 2.46 |
| HGV-2 | $C_2H_5$ | OH | $C_2H_5$ | 1.97 |
| HGV-5 | $OCH_3$ | OH | $OCH_3$ | 1.7 |
| HGV-6 | Cl | OH | Cl | — |

-continued

| Molecule | R¹ | R² | R³ | IC 50 (microM) |
|---|---|---|---|---|
| PGV-1 | $CH_3$ | OH | $CH_3$ | 2.20 |
| PGV-2 | $C_2H_5$ | OH | $C_2H_5$ | 2.21 |
| PGV-5 | $OCH_3$ | OH | $OCH_3$ | 0.99 |
| PGV-6 | Cl | OH | Cl | 14.89 |
| PGV-0 | $OCH_3$ | OH | $OCH_3$ | 6.4 |
| GVT-6 | Cl | OH | Cl | — |

ANTI BATERIAL AND ANTIFUNGAL ACTIVITY TEST

Sterile medium of Bacto Muller Hinton was melted at 45-50° C. and poured (25 ml) into a sterile Petric dish (100 mm in diameter), and was left at room temperature for 1 hour. The sterility was checked by overnight incubation (37° C.). The media was immediately used. The microorganism used was gram positive and gram negative. The drug solutions of 0.1, 0.2 and 0.4% in DMSO were used. Incubation was performed at 37° C. for 24 hours. Zone of inhibition induced by active compound was measured in millimeter, and was compared with DMSO, nipagin and curcumin on the growth of E. Coli, S. aureus, S. pneumoniae, B. subtilis, and C. albican.

| | Minimum Inhibition Concentration (%) | | |
|---|---|---|---|
| Microorganism | HGV-6 | PGV-6 | GVT-6 |
| 1. *S. Aureus* | 0.35 | 0.25 | 0.25 |
| 2. *S. pheumoniae* | 0.05 | 0.10 | 0.05 |
| 3. *B. subtilis* | 0.25 | 0.20 | 0.30 |
| 4. *C. albicans* | 0.25 | 0.25 | 0.25 |

PART OF SYNTHESIS PROCESS

Example HGV-1

To 1 part of cyclohexanone and 1 part of an aldehyde were added hydrochloride acid as a catalyst and stirred at 20-50° C. for sometime, and left for several days at ambient temperature. The yield was macerated with glacial acetic acid and water, filtered, and yield was purified by crystallization with ethanol-water.
Melting point 225-226° C.
Rendement 85%.
NMR (DMSO-d6)
1,72 (quintet, 2H, C-$CH_2$-C); 2,24 (s, 12H, -$CH_3$); 2,88 (t, 4H, $H_2$C-C-$CH_2$); 7,16 (s, 4H, arom); 7,52 (s, 2H, -CH=); 8,78 (s, 2H, -OH).
HRMS ($C_{24}H_{26}O_3$) obtained 362,1875; calculated 362, 1882.

The same procedure was conducted to prepare HGV-2.
Melting point 197-198° C.
Rendement 81%.
NMR (DMSO-d6)
1,17 (t, 12H, -$CH_3$); 1,75 (quintet, 2H, C-$CH_2$-C); 2,65 (q, 8H, C-$CH_2$-Ar); 2,9 (t, 4H, $H_2$C-C-$CH_2$); 7,18 (s, 4H, arom); 7,56 (s, 2H, -CH=); 8,7 (s, 2H, -OH).
HRMS ($C_{28}H_{34}O_3$) obtained 418,2508; calculated 418, 2508.

The same procedure was conducted to prepare HGV-5.
Melting point 134-135° C.
Rendement 44%.
NMR (DMSO-d6)
1,76 (quintet, 2H, C-$CH_2$-C); 2,96 (t, 4H, $H_2$C-C-$CH_2$); 3,83 (s, 12H, $OCH_3$); 6,86 (s, 4H, arom); 1,60 (s, 2H, -CH=); 8,5-9,2 (br, 2H, -OH).
HRMS ($C_{24}H_{26}O_7$) obtained 426,1765; calculated 426, 1678.

The same procedure was conducted to prepare HGV-6.
Melting point 201-202° C.
Rendement 43%.
NMR (DMSO-d6)
1,71 (quintet, 2H, C-$CH_2$-C); 2,84 (t, 4H, $H_2$C-C-$CH_2$); 7,46 (s, 2H, -CH=); 7,56 (s, 4H, arom); 10,65 (br, 2H, -OH).
HRMS ($C_{20}H_{14}O_{14}$) obtained 441,9699; calculated 441, 9697.

The same procedure was conducted to prepare PGV-1.
Melting point 269-270° C.
Rendement 78%.
NMR (DMSO-d6)
2,24 (s, 12H, -$CH_3$); 3,04 (t, 4H, $H_2$C-$CH_2$); 7,28 (s, 6H, arom and -CH=); 8,92 (br, 2H, -OH).
HMRS ($C_{23}H_{24}O_3$) obtained 348,1729; calculated 348, 1725.

The same procedure was conducted to prepare PGV-2.
Melting point 193-194° C.
Rendement 92%.
NMR (DMSO-d6)
1,17 (t, 12H, -$CH_3$); 2,64 (q, 8H, -$CH_2$-Ar); 3,03 (s, 4H, $H_2$C-$CH_2$); 7,30 (s, 4H, arom); 7,32 (s, 2H, -CH=); 8,82 (br, 2H, -OH).
HRMS ($C_{27}H_{32}O_3$) obtained 404,2348; calculated 404, 2351.

The same procedure was conducted to prepare PGV-5.
Melting point 226-227° C.
Rendement 79%.
NMR (DMSO-d6)
3,14 (s, 4H, $H_2$C-$CH_2$); 3,86 (s, 12H, -$OCH_3$); 7,00 (s, 4H, arom); 7,40 (s, 2H, -CH=); 9,12 (br, 2H, -OH).
HRMS ($c_{23}H_{24}O_7$) obtained 412,1519; calculated 412,1522.

The same procedure was conducted to prepare PGV-6.
Melting point 260-262° C.
Rendement 47%.
NMR (DMSO-d6)
3,04 (s, 4H, $H_2$C-$CH_2$); 7,32 (s, 2H, -CH=); 7,68 (s, 4H, arom); 10,81 (br, 2H, -OH).
HRMS ($C_{19}H_{12}O_3Cl_4$) obtained 427,9540; calculated 427, 9541.

The same procedure was conducted to prepare PGV-0.
Melting point 212-214° C.
Rendement 97%.
NMR (DMSO-d6)
3,61 (s, 4H, $H_2$C-$CH_2$); 4,51 (s, 6H, -$OCH_3$); 7,42 (d, 2H, J=8Hz, $H_5$); 7,7 (d, 2H, J=8Hz, $H_6$); 7,75 (s, 2H, $H_2$); 7,83 (s, 2H, -CH=); 8,79 (s, 2H, -OH).
HRMS ($C_{12}H_{20}O_5$) obtained 352,130; calculated 352,1311.

The same procedure was conducted to prepare GVT-6, which is 1,5-bis (4-hydroxy- 3,5-dichlorophenyl)-1,4-pentadiene-3-one.
Melting point 255-256° C.
Rendement 56%
NMR (DMSO-d6)
7,28 (d, 2H, -C=CH-CO-); 7,68 (d, 2H, -CH=C-CO-); 7,86 (s, 4H, arom); 10,82 (br, 2H, -OH).
HRMS $C_{17}H_{10}O_2C_{14}$) obtained 401,9382; calculated 401, 9384.

What is claimed is:

1. A compound represented by the formula:

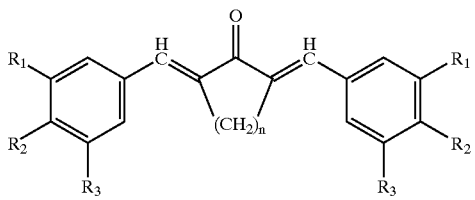

wherein n is an integer from 0 to 3, and $R_1$, $R_2$ and $R_3$ are each independently selected from the group consisting of methyl, ethyl, isopropyl, tertiary butyl, hydroxy, chloro, trifluoromethyl, methoxy, and dimethylamine, with the provisos that:
   (i) when n is 2, $R_1$ and $R_3$ are not both methyl or methoxy;
   (ii) when n is 2, $R_1$ is not chloro if $R_3$ is methoxy; and
   (iii) when n is 2 or 3, $R_1$ $R_3$ are not both tertiary butyl.

2. The compound according to claim 1, wherein n is 3, $R_1$ and $R_3$ are methyl, and $R_2$ is OH.

3. The compound according to claim 1, wherein n is 3, $R_1$ and $R_3$ are ethyl, and $R_2$ is OH.

4. The compound according to claim 1, wherein n is 3, $R_1$ and $R_3$ are methoxy, and $R_2$ is OH.

5. The compound according to claim 1, wherein n is 3, $R_1$ and $R_3$ are chloro, and $R_2$ is OH.

6. The compound according to claim 1, wherein n is 2, $R_1$ and $R_3$ are ethyl, and $R_2$ is OH.

7. The compound according to claim 1, wherein n is 2, $R_1$ and $R_3$ are methoxy, and $R_2$ is OH.

8. The compound according to claim 1, wherein n is 2, $R_1$ and $R_3$ are chloro, and $R_2$ is OH.

9. The compound of claim 1, wherein $R_2$ is OH.

10. A method for preparing a compound of claim 1, the method comprising: forming a reaction mixture comprising a benzaldehyde compound, a ketone compound, and a catalyst; the benzaldehyde compound being represented by the formula:

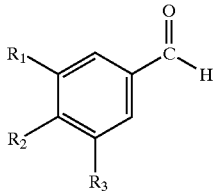

wherein $R_1$, $R_2$ and $R_3$ are each independently selected from the group consisting of methyl, methoxy, ethyl, isopropyl, tertiary butyl, hydroxy, chloro, trifluoromethyl, and dimethylamine;

and the ketone compound being represented by the formula:

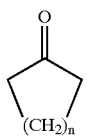

wherein n is an integer from 0 to 3; and
   reacting the benzaldehyde compound and the ketone compound to thereby form a compound of claim 1, with the provisos that:
   (i) when n is 2, $R_1$ and $R_3$ are not both methyl or methoxy;
   (ii) when n is 2, $R_1$ is not chloro if $R_3$ is methoxy; and
   (iii) when n is 2 or 3, $R_1$ and $R_3$ are not both tertiary butyl.

11. The method of claim 10, wherein the benzaldehyde compound is 3,5-dimethyl-4-hydroxy benzaldehyde.

12. The method of claim 11, wherein the ketone compound is cyclohexanone.

13. The method of claim 10, wherein n is 2 or 3; $R_1$ and $R_3$ are selected from the group consisting of methyl, ethyl, methoxy, chloro; and $R_2$ is OH.

14. The method of claim 10, wherein at least one of $R_1$, $R_2$, and $R_3$ is chloro.

15. The method of claim 10, wherein said reaction mixture comprises tertrahydrofuran as a solvent.

16. The compound represented by the formula:

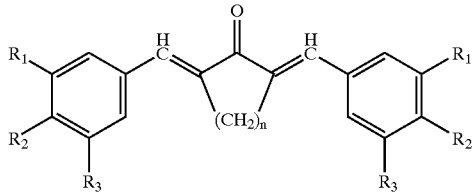

wherein n is an integer from 0 to 3, and $R_1$, $R_2$ and $R_3$ are each independently selected from the group consisting of methyl, ethyl, isopropyl, tertiary butyl, hydroxy, chloro, trifluoromethyl, methoxy, and dimethylamine, wherein at least one of $R_1$, $R_2$, and $R_3$ is chloro, provided that when n is 2, $R_1$ is chloro, $R_2$ is hydroxy, the $R_3$ is not methoxy.

17. The compound of claim 16, wherein n is 3, $R_1$ and $R_3$ are chloro, and $R_2$ is OH.

18. The compound of claim 16, wherein n is 0, $R_1$ and $R_3$ are chloro, and $R_2$ is OH, which is 1,5-bis(4-hydroxy-3,5-dichlorophenyl)-1,4-pentadiene-3-one.

* * * * *